United States Patent [19]
Petersen et al.

[11] Patent Number: 5,606,590
[45] Date of Patent: Feb. 25, 1997

[54] SURGICAL LASER BEAM-BASED ALIGNMENT SYSTEM AND METHOD

[76] Inventors: Thomas D. Petersen, 9680 Alto Dr., La Mesa, Calif. 91941; Richard J. Harp, 2122 Subida Ter., Carlsbad, Calif. 92009

[21] Appl. No.: 375,425

[22] Filed: Jan. 18, 1995

[51] Int. Cl.$^6$ ............................................. A61B 6/08
[52] U.S. Cl. ............................................. 378/177; 378/206
[58] Field of Search ........................... 378/206, 205, 378/204, 180, 167, 170, 177, 193, 208, 209

[56] References Cited

U.S. PATENT DOCUMENTS

| | | | |
|---|---|---|---|
| 3,648,305 | 3/1972 | Ersek | 378/180 |
| 3,947,689 | 3/1976 | Wagner | 378/206 X |
| 4,349,917 | 9/1982 | Moore | 378/164 |
| 4,426,726 | 1/1984 | Cheetham | 378/206 |
| 4,836,671 | 6/1989 | Bautista | 378/206 |
| 5,166,968 | 11/1992 | Morse | 378/180 X |
| 5,222,115 | 6/1993 | Highgenboten | 378/177 |
| 5,241,578 | 8/1993 | MacMahon | 378/206 X |

*Primary Examiner*—David P. Porta
*Attorney, Agent, or Firm*—H. Jay Spiegel

[57] ABSTRACT

A surgical alignment system employs a laser beam generating device and a lens system to convert the beam into a plane of light which is aligned along a desired axis of the human body to provide proper alignment to the surgeon to enhance the accuracy of orthopedic surgery such as total knee, hip or back surgery. The laser beam generating device is mounted on a bracket which is fixed to a cassette holder positioned beneath the patient and having a chamber designed to removably receive an x-ray film cassette. The cassette holder is made of a material which is transparent to x-rays. Straps incorporated into the cassette holder are designed to fix the patient to the cassette holder during surgery. The cassette holder includes a radio-opaque indicator with the bracket holding the laser beam generating device having a second radio-opaque indicator so that when an x-ray is taken of the patient affixed to the inventive device, compensation for parallax may be carried out.

25 Claims, 12 Drawing Sheets

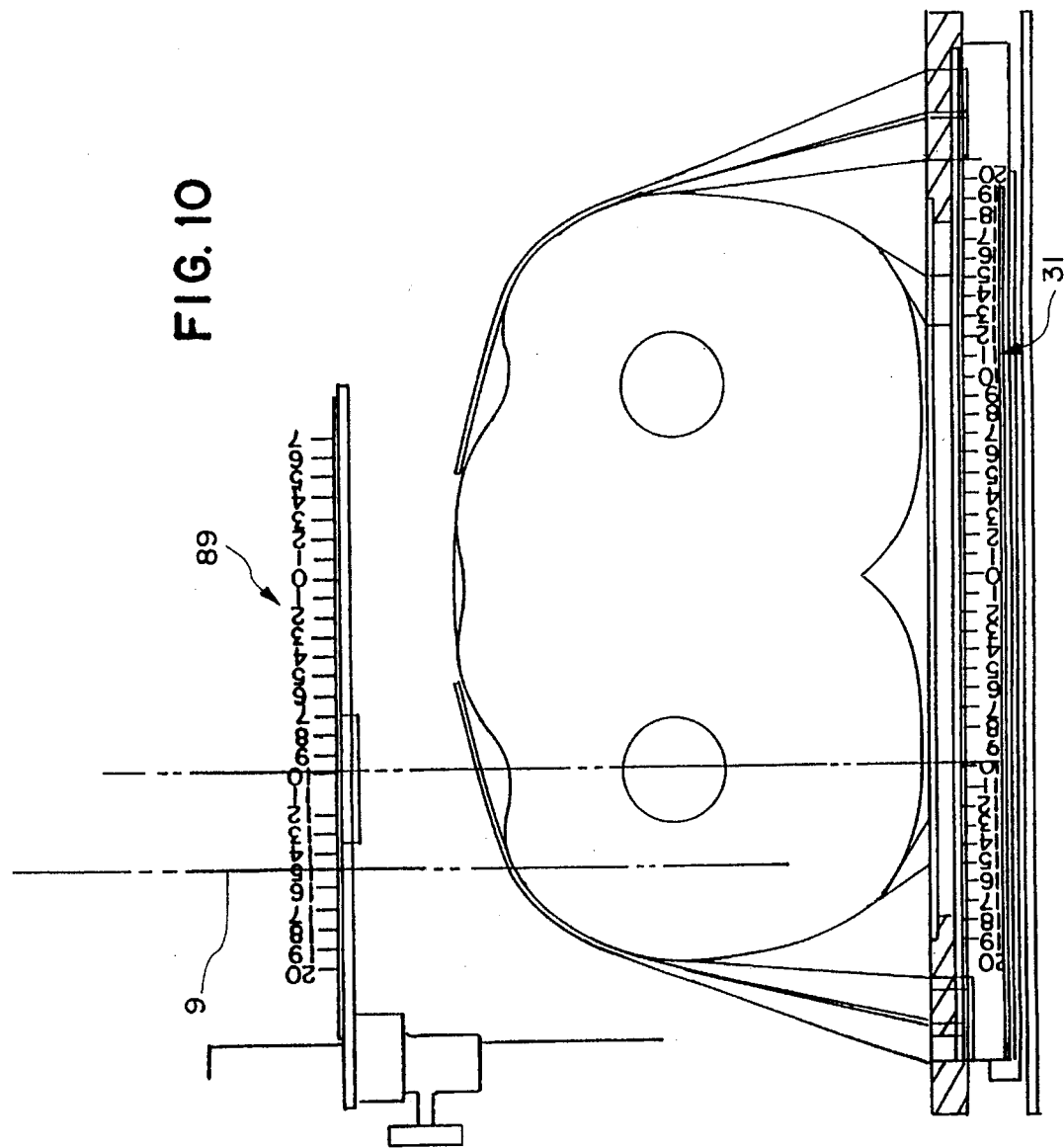

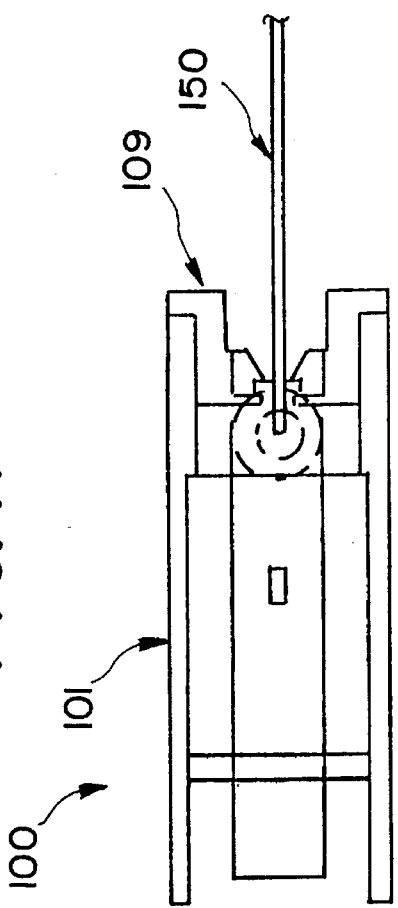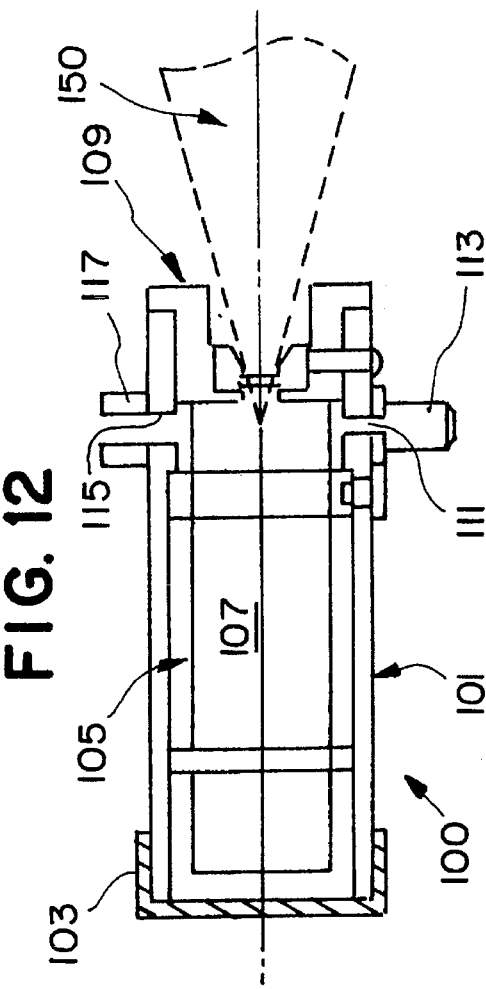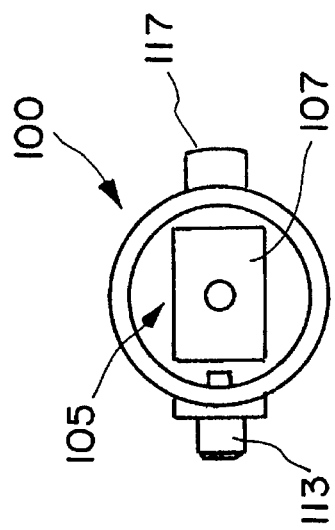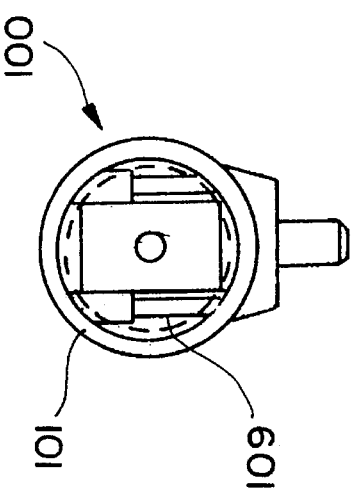

SURGICAL LASER BEAM-BASED ALIGNMENT SYSTEM AND METHOD

BACKGROUND OF THE INVENTION

The present invention relates to a surgical laser beam-based alignment system and method including the use of a narrow, straight beam of light from a low voltage laser device to determine correct alignment in total knee, hip and back surgery. In orthopedic surgery it is essential that correct alignment be obtained for successful results. It is well known that failure to correctly align a total knee arthroplasty, for example, leads to premature failure of the prosthesis. In the past, extramedullary rods, intramedullary rods and flexible cords have been used to assist the surgeon in this important task. These methods all have their potential problems and can lead to failure or injure the patient. In the case of the extramedullary alignment method, the center of the femoral head has to be radiologically determined and marked externally on the patient. The use of trial and error to find the center of the femoral head and accurately locate the external marker on the patient is time-consuming. Also, improper positioning of the x-ray machine with respect to the center of the femoral head and the distance from the x-ray machine to the radiographic cassette introduces the error factor known as "parallax". Also, alignment rods presently used have to be extended away from the center of the rotation of the bone and, consequently, there can be a significant error with any rotation of the distal femur from neutral. For these reasons, extramedullary alignment of the distal femur fell out of favor in the late 1980s and the intramedullary rod alignment system became popular. With the intramedullary rod, the rod is placed through a drill hole in the intracondylar notch into the femoral canal and a predetermined difference between the anatomical axis of the femur and the mechanical axis, the so-called tibial femoral angle, is dialed in by mechanical means and the perpendicular cut is then made through the transverse axis. Unfortunately, there are a number of inherent errors in intramedullary alignment means. Not uncommonly, the intramedullary canal is quite large in diameter and the rod can be misaligned up against one cortex or the other. An error caused by a large intramedullary canal can be up to 2–3 degrees. Because the intramedullary rod is hidden from the surgeon's view, he has no way of determining this inherent error. Also, the intramedullary canal in the sagittal plane is curvalinear, and can cause mispositioning of the rod depending upon the location of the entrance hole, either in the anterior or posterior direction, causing the rod to be an inaccurate means of determining a perpendicular cut on the femur in the sagittal plane. It is becoming apparent that intramedullary rods can be dangerous and even lethal when used to align a total knee resection. Recent studies have shown a tremendous release of fat emboli into the circulation upon release of the tourniquet after total knee arthroplasty. A number of deaths have been reported secondary to this complication. Ideally, a reliable, non-invasive extramedullary system would be much safer for the patient.

It is with these issues in mind that the present invention was developed.

SUMMARY OF THE INVENTION

The inventive system portrayed herein effectively resolves the following surgical problems:

1. Locating the center of the femoral head to within a small range of error with a single x-ray exposure;

2. Parallax error in the x-ray system;

3. Difficulty of adjusting the patient to the x-ray film and cassette;

4. Difficulty adjusting the x-ray film to all operating tables;

5. Difficulty obtaining a clear x-ray image through a substantial cassette that must support a 200–300 pound patient;

6. Difficulty obtaining a clear, narrow beam of light in a single plane;

7. Sterility issues when employing a non-autoclavable low voltage laser device;

8. Accurate adjustment and calibration of the laser;

9. Safety for the operating room personnel; and

10. Interoperative adjustment for inaccurate resection.

The present invention relates to an improved extramedullary alignment device in the nature of a surgical laser beam-based alignment system and method and is related to co-applicant Petersen's previous alignment assist device as disclosed in U.S. Pat. No. 4,524,766. In this previous patent, use of radiographically opaque L arm located over the patient's femoral head was described. The device that is disclosed herein is an improvement over this patented device and uses a low voltage laser light plane instead of a flexible cord for the alignment and subsequent resections. This application specifically addresses problems with the prior art system and introduces new, unique solutions to problems recognized but not addressed or solved in the previous patent. In an extramedullary alignment system, the center of the femoral head must be located externally and non-invasively on the patient. The only reliable method of doing so is through the use of x-ray equipment. In accomplishing this task, a locating device must be positioned over the femoral head by the surgeon guessing at the approximate location using bony landmarks. Unfortunately, many patients are very obese and these bony landmarks are obscured. Consequently, this locating device, which may comprise a pointer arm, is frequently an unreliable indicator of femoral head location when the x-ray is obtained.

This problem was partially solved by co-applicant Petersen's prior U.S. Pat. No. 4,524,766 through inclusion of a radiographically opaque scale that shows up on an x-ray so that the locating means (pointer arm) could be moved to the correct location. However, this required that the x-ray machine be located over the actual femoral head, the location of which was being guessed at. This introduced an error factor called "parallax". Parallax occurs where the x-ray beam generator is misaligned with respect to the femoral head so that the angular relationship between the locating device, the femoral head and the x-ray beam generator causes the locating device to be displayed on the x-ray, with respect to the femoral head, in an inaccurate manner, displaced from its actual location. The present invention overcomes the resultant error factor by including two scales, a first scale that holds the locating pointer arm above the patient and a second scale incorporated into the cassette holder below the patient but just above the x-ray film. Due to the fact that the patient's femoral head is approximately midway between the top scale and the bottom scale, a mean of the two numbers on the scales where the x-ray shows the femoral head can be used for the actual number and location of the center of the femoral head. This clearly defines the parallax error and adjusts for it.

To increase accuracy even further, a first x-ray can be shot from the side of the patient to allow exact measurement of the vertical distances between each scale and the femoral head. Subsequently, the first scale can be lowered or raised to equalize these distances. Thereafter, the second x-ray, from above, can be taken.

Also, in the prior art, the x-ray cassette is placed in the radiographic slot between the Bakelite material and the operating table. The cassette is slid-in awkwardly from the top of the table because of the very large size of the cassette and is then retrieved in an awkward manner. This problem has been solved by designing a cassette holder that fits on top of the operating table and is readily accessible to the x-ray technician.

An additional problem involves locating the pointer arm so that it lies just above the femoral head, especially on obese patients. This necessitated designing a locating device that fits into a specific position on the film holding cassette so that when the patient is placed onto the cassette, while being positioned on the operating table, the position of the patient would be determined by flexing the patient's knee to 90° on the operative side and striking the positioning device at that prescribed angle. Subsequently, the surgeon would adjust the position of the cassette and the radiographic L arm, and all subsequent positions of the film, radio-opaque rulers, etc., would be in appropriate positions. Lastly, the cassette would have to be of substantial strength to hold the weight of a 250–300 pound patient. This necessitates a certain thickness and strength. Applicants have discovered that a strong, durable graphite material is virtually transparent to x-rays, thus providing a clear image of the operative hip. Graphite has relatively low mass and low molecular weight. Thus, x-rays pass therethrough with little velocity reduction. The chosen graphite material is a cloth woven of flat ribbons of rectangular cross-section with no appreciable air gaps. Layers of cloth are stacked in overlapping staggered fashion absolutely precluding the existence of straight air gaps. To protect the patient, surgeon and other personnel, a layer of fiberglass covered with resin covers the graphite material to preclude slivers. This same material is extremely strong and is able to support a patient regardless of their weight.

Another problem in the prior art is the fact that the patient's femoral head tends to move during the operative procedure with tugging, pulling and flexing of the knee necessary to perform the operation. This requires a method to stabilize the patient to the x-ray cassette. Applicants devised a method of using two straps that extend from the midsacral area of the patient at an angle of 30° and extend over the iliac crest of the patient and cross over the pelvis and attach back on themselves in a crisscross manner that rigidly fixes the pelvis to the cassette. Even if the patient is pushed and pulled with these rigid strap systems, the cassette moves with the patient and the accuracy of the locating device is maintained.

The present invention employs a low voltage, Class 3A diode crystal laser. This laser has several unique features that create a very brilliant red, narrow plane of light that can be used by the surgeon as a referencing device for optimal alignment. This diode crystal laser puts out a monochromatic beam of light that is approximately 1 mm×1.5 mms and cylindrical in shape. It is collimated through a series of lenses to a cylinder of light that is further split by a line generator lens to a plane of light that is approximately 30° in angulation by 1 mm in width. This creates a very precise, accurate line from which the orthopedic surgeon can reference his resection cuts. (The plane of laser light is aligned to be vertically plumb.)

The diode of preference is approximately 635 nanometers or lower range which provides a brilliant red light to the human eye. The lower the range in nanometers, the more brilliant the light. This system also employs a solid-state regulator that regulates the voltage to 4½ volts even though the power source may be of higher voltage. This provides 6–8 hours of even, brilliant line demarcation that does not diminish in power throughout the operative case. The solid-state regulator is important because the diode crystal is very sensitive to voltage irregularities. This system is self-contained with a self-contained power source so that no external cords are necessary.

The diode crystal and the power source are both sensitive to heat and steam and therefore autoclaving of the laser itself is not possible. Consequently, a sterilizable cylinder with appropriate lenses has been developed along with an alignment system permitting the laser to be aligned within the cylinder. A sterilized top that goes on top of the laser as it is inserted into this cylinder maintains sterility. Alignment of the laser beam is critical, since misalignment affects accuracy of the beam. Installation of the laser device into the sterilized cylinder has been simplified by providing the cylinder at a length so that the laser can still be handled by two fingers outside the sterilized cylinder without touching the edge of the cylinder. Also, the alignment channel that the laser fits into is easily located on the top edge of the cylinder and can be readily located by the circulating nurse. The nurse simply drops the laser over the alignment rod and slips it into the cylinder until it strikes bottom. The operating room technician then puts the sterile cap onto the cylinder locking it onto the two locking pins.

The present invention includes a negative vacuum system that is applied to the internal chamber of the laser cylinder. It provides a negative vacuum to the inside of the cylinder that in turn accomplishes the following:

1) The laser diode crystal generates heat and this heat is transferred to the lens and excessive heat can damage the lenses, affecting the accuracy of the light beam, and can also damage the diode crystal. The generation of heat also causes expansion of critically aligned micro-optical components, such as the light emitting laser diode itself and its mounting structure, and the expansion and misalignment of the collimating lens system and their supportive mounts, and the line generating lens and its supportive mounts. All expansion from temperature increases results in beam "wander" and inaccuracy.

2) In autoclaving the cylinder cannister, fluid may frequently be left in the cylinder and when this fluid is heated by activation of the diode, the water will vaporize and cloud the lens system distorting the laser beam.

3) Introducing a nonsterile laser into the cylinder inner chamber sterile environment requires a negative vacuum be applied so that a non-airtight cannister will not allow any bacterium to escape.

All of these problems are solved by Applicants by applying a negative vacuum attached through a connection to the top of the laser cannister. A filtered opening on the undersurface of the laser allows for ingress of air across the lenses in the cannister. This structure creates a negative vacuum that brings in air conditioned, cooled air into the laser thereby cooling the laser, the diode and the lenses. This prevents fogging of water residue.

Safety features have been built into the laser system to prevent operating personnel from damaging their eyes if they were to put the laser directly up to their eye. The laser has been deliberately recessed one inch from the outer orifice at the bottom of the cylinder to prevent any of the operating room personnel from putting the laser directly up to their eye. A beam of only 4 mw of power will not damage the eye one inch from the lens. It is highly unlikely that anyone would do this, but this safety feature has been designed into this laser system.

The accuracy of the laser device is multifactorial. There are two adjustment knobs on the laser cylinder, one for up and down angulation and one for side-to-side angulation. By eliminating the side-to-side angulation, the patient can be theoretically moved superiorly and inferiorly on the operating table without any loss of accuracy. The laser is therefore calibrated after the x-ray is obtained and the pointer arm is located directly over the femoral head. The laser is attached with a bracket directly on top of the locator arm bracket. The bracket is tightened to the locating arm base and then the laser is calibrated. The laser light is directed down at the locating arm and the side-to-side knob is tightened when the laser light hits the midportion of the locating arm. This eliminates the side-to-side plane of inaccuracy. The light is then moved up and down until it strikes the midthigh and extends all the way to the ankle of the patient. The laser knobs are then tightened and stay in this position throughout the operative case.

The most important feature of this invention is the assistance the straight line alignment beam gives the orthopedic surgeon in determining whether his resection cuts were accurate. The surgeon, after the alignment cuts are made on bone, can press the two alignment cuts together firmly and align the leg on the alignment beam. If the cuts are made correctly, the beam will extend through the midportion of the knee and the midportion of the ankle, thus reconstructing the mechanical axis from the center of the femoral head to the center of the knee to the center of the ankle. This represents neutral alignment, the desired result. If the alignment is not correct when the resection surfaces are lined up, now is the time to correct the alignment with additional resections. The trial components can be applied and the knee similarly aligned and again the alignment can be checked. Lastly, final adjustment can be done during the cement procedure, if cement is used.

As such, it is a first object of the present invention to provide a surgical laser beam-based alignment system and method.

It is a further object of the present invention to provide such a system including a laser beam generating device accompanied with a lens system converting the beam to a plane of light.

It is a yet further object of the present invention to provide such a device including a cassette holder designed to be positioned beneath the patient, to receive x-ray film and to be made of a material transparent to x-rays.

It is a yet further object of the present invention to provide such a device including such a cassette holder incorporating rigid straps and a strap fixing system allowing the patient to be fixedly strapped to the cassette holder.

It is a still further object of the present invention to provide such a device including means for compensating for parallax.

It is a yet further object of the present invention to provide such a device including a cylinder designed to contain the laser beam generating device and including a vacuum system designed to prevent contamination of the patient from bacterium as well as to evaporate any liquid vapor which is located within the cylinder after sterilization.

These and other objects, aspects and features of the present invention will be better understood from the following detailed description of the preferred embodiment when read in conjunction with the appended drawing figures.

BRIEF DESCRIPTION OF THE DRAWINGS

FIG. 10 shows a cross-sectional view similar to that of FIG. 4 but with the two scales as well as the laser beam generating device L-shaped mounting bracket depicted.

FIG. 11 shows a cross-sectional top view of the laser beam generating device and associated lens and housing.

FIG. 12 shows a cross-sectional side view of the structure of FIG. 11.

FIG. 13 shows a rear view of the structure of FIGS. 11 and 12.

FIG. 14 shows a front view of the structure of FIGS. 11 and 12.

SPECIFIC DESCRIPTION OF THE PREFERRED EMBODIMENT

Figure 1:
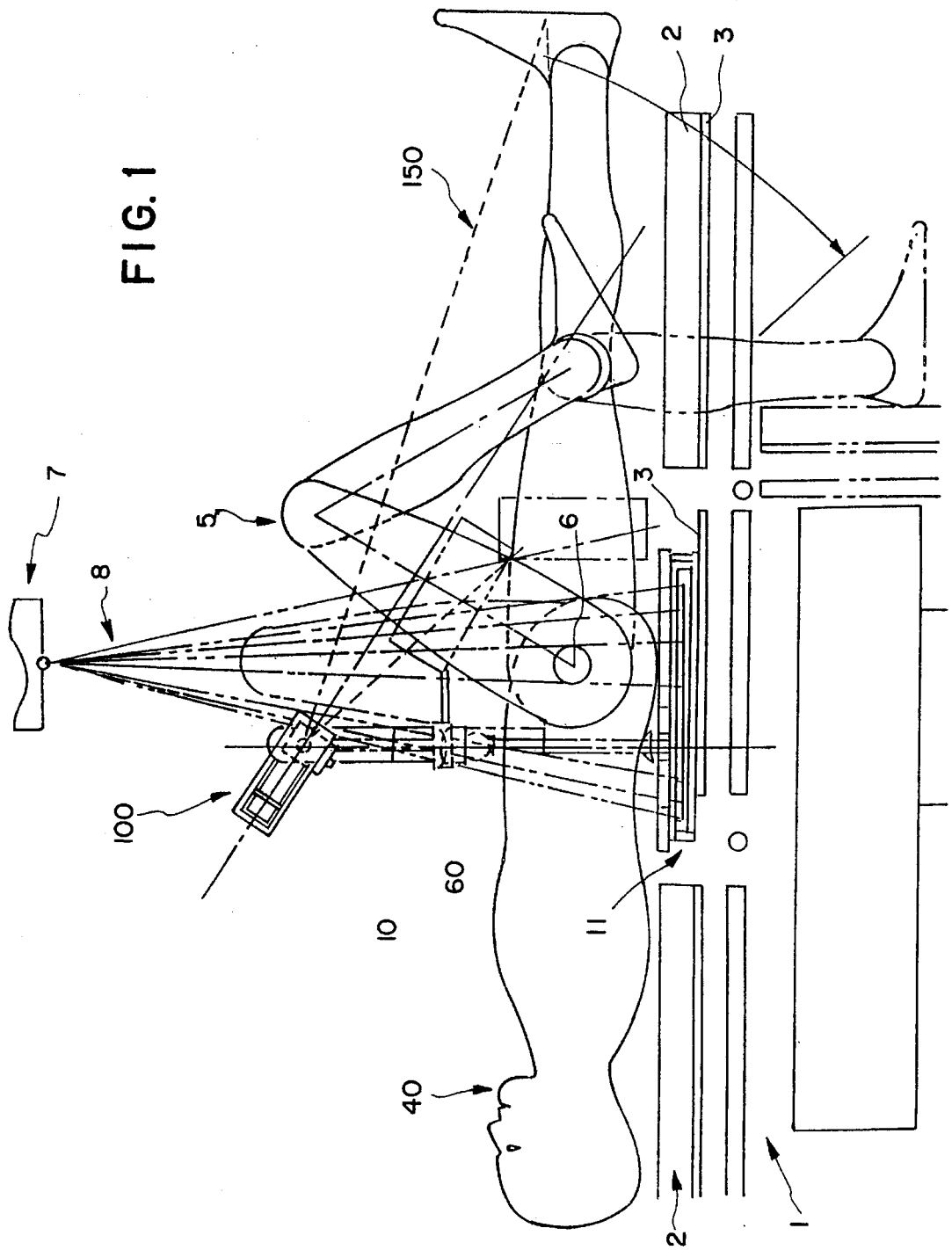
FIG. 1 shows a side view of the present invention including depiction of a typical operating table and an outline of a patient appropriately positioned.

With reference, first, to FIG. 1, an operating table is generally designated by the reference numeral 1 and is seen to include a foam pad 2 on top of a rigid support surface 3. As is seen in FIG. 1, a portion of the foam pad 2 has been removed so that pertinent structures of the present invention may be placed directly on the support surface 3. The features of the operating table as described above are conventional and form no part of the present invention.

The present invention is generally designated by the reference numeral 10 and is seen to include a cassette holder generally designated by the reference numeral 11, an L-shaped support arm system 60 and a laser beam generating device 100. As also shown in FIG. 1, the patient 4 has a right leg 5, the knee of which is to be the subject of surgery in the example shown. Shown in FIG. 1 is the center 6 of the femoral head of the right leg of the patient 4. This center 6 is also depicted, in particular, in FIG. 2.

Figure 2:
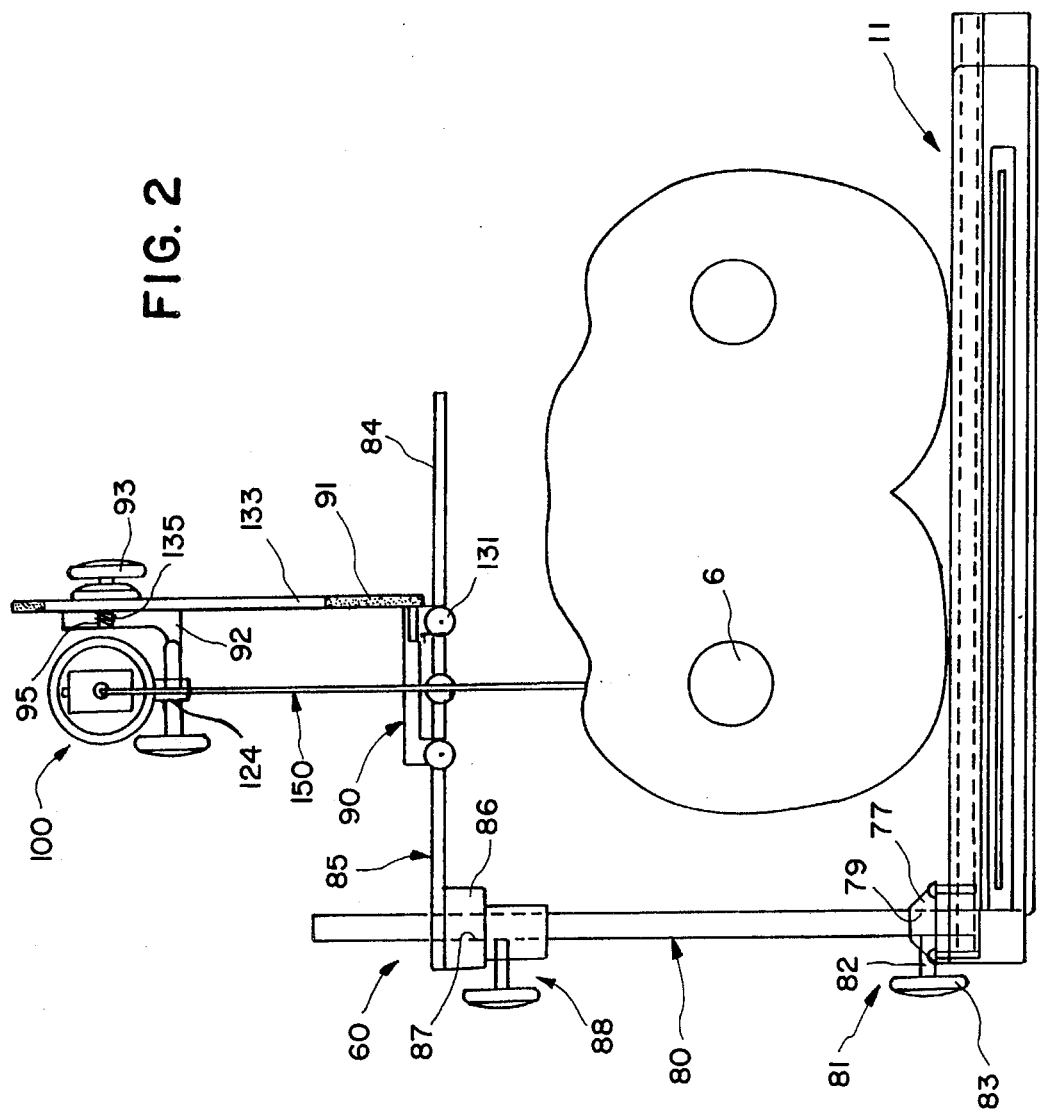
FIG. 2 shows an end view, partially in cross-section, of the present invention looking from the foot of the patient toward the head thereof and showing the plane of light emanating from the laser beam generating device.

FIG. 1 also depicts a plane of light 150 emanating from the laser beam generating device 100. This plane of light 150 is also depicted in FIG. 2. As also shown in FIG. 1 and as better understood with further reference to FIG. 2, the location on the leg 5 of the patient 4, where the plane of light 150 impinges on the leg 5, draws a line down the leg of the patient in a manner as aligned by the surgeon. For example, the surgeon can align the plane of light 150 so that a line of light is drawn down the mechanical axis of the leg 5 of the patient 4.

With further reference to FIG. 1, an x-ray machine is generally depicted with the reference numeral 7 and this x-ray machine generates a beam 8 of x-ray radiation which emanates conically about a center line 9 which is best seen in FIG. 10. FIG. 10 shows the situation where the center line 9 of the x-ray beam 8 is offset from the center line of the femoral head thereby causing parallax error. Applicants' solution to parallax error will be described in greater detail hereinafter.

With reference, now, to FIGS. 3–7, certain details concerning the cassette holder 11 will be described in more detail.

Figure 3:
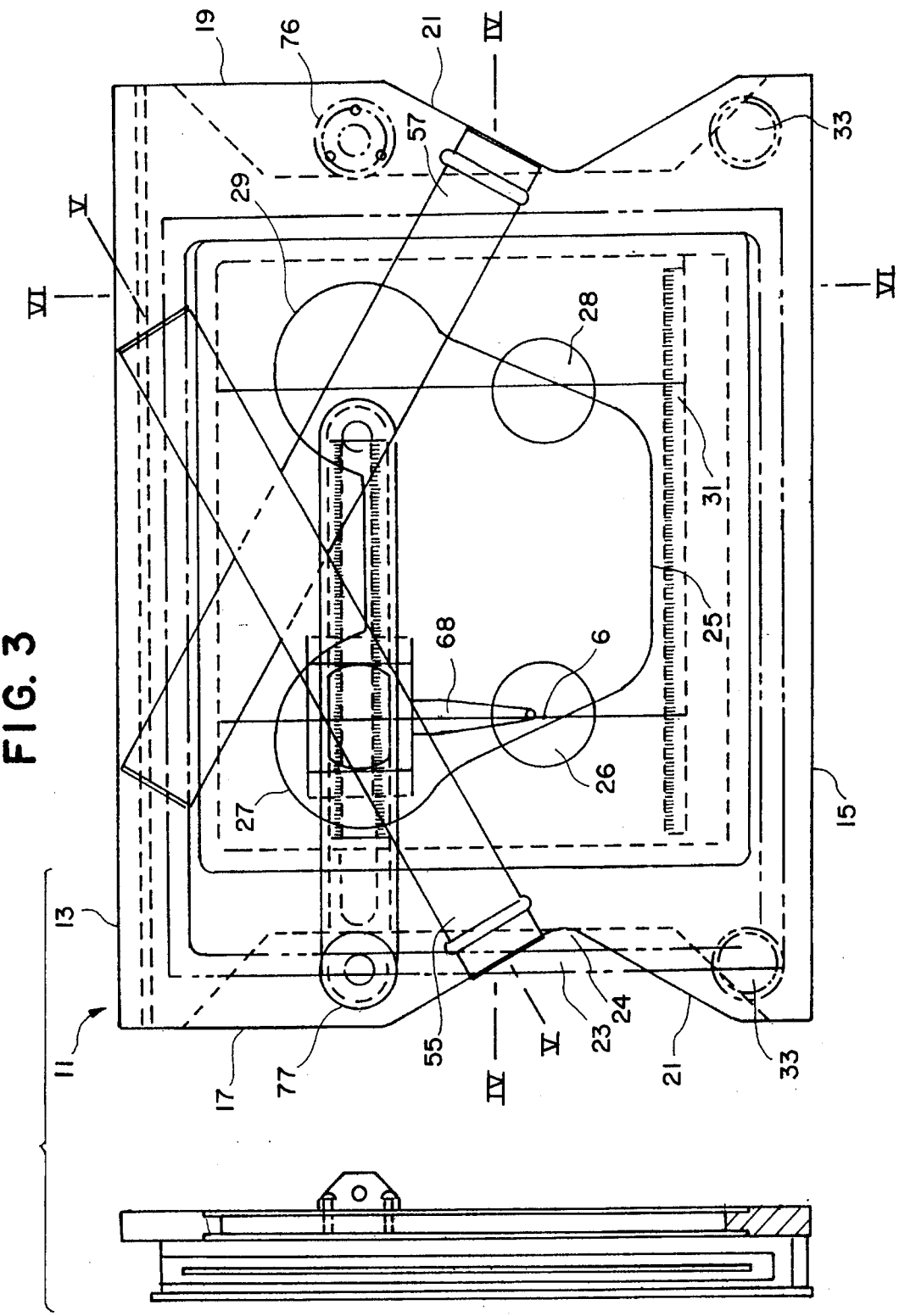
FIG. 3 shows a top view of the cassette holder of the present invention.

With reference to FIG. 3, the cassette holder 11 has a generally rectangular configuration including a proximal wall 13, a distal wall 15 and side walls 17 and 19, respectively. As is seen in FIG. 3, the side walls 17 and 19 each have a generally triangular notch 21 therein which is provided to allow the surgeon to easily insert and remove an x-ray film cassette shown in FIGS. 3 and 6 and designated by the reference numeral 23 which contains the x-ray film 24. An outline of the pelvic region of the patient is generally designated by the reference numeral 25 and is seen to include, pertinently, a visualization of the iliac crests 27 and 29 as well as the femoral heads 26 and 28 of which the femoral head 26 has the center 6 corresponding to that which is depicted in FIGS. 1 and 2.

Figure 6:
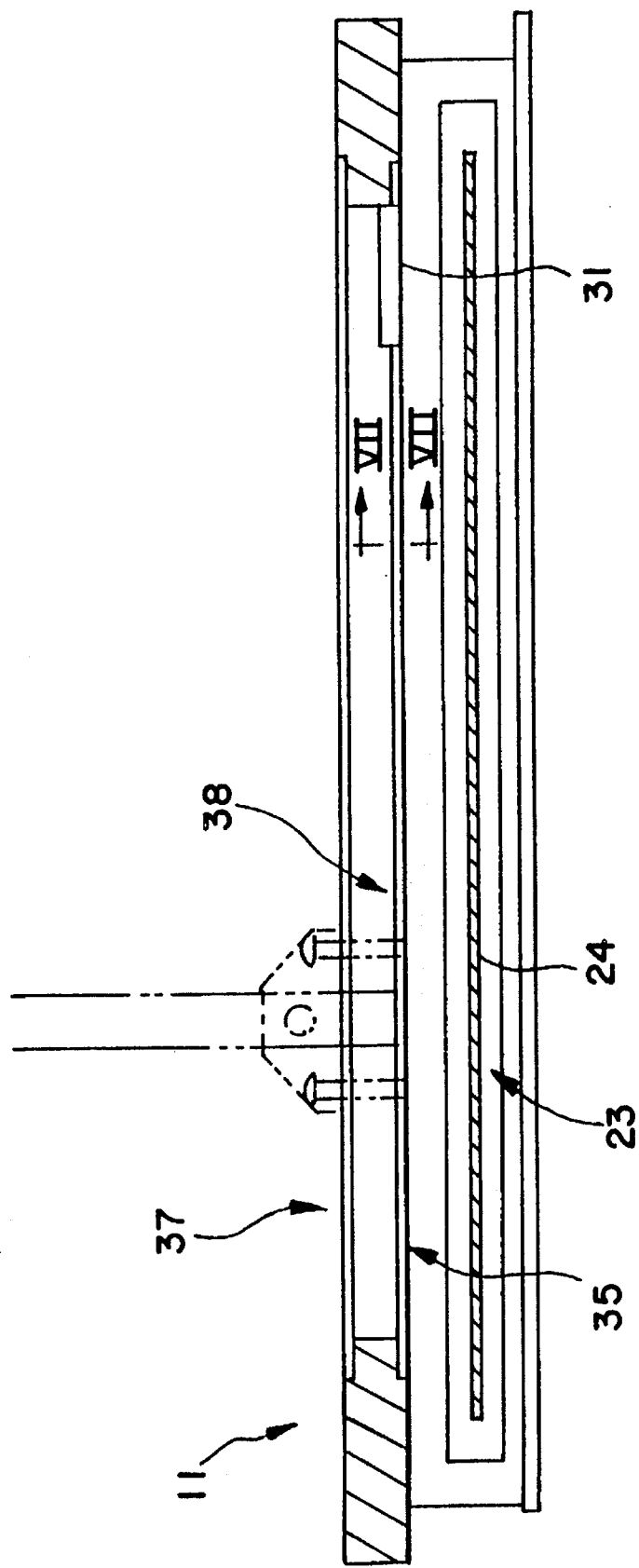
FIG. 6 shows a cross-sectional view along the line VI—VI of FIG. 3.

With further reference to FIG. 3, it is seen that a radio-opaque indicator 31 is embedded within the cassette holder 11. The particular location of the radio-opaque indicator is best seen in FIG. 6. In a further aspect, leveling devices 33 are provided in two of the corners of the cassette holder 11 and include a chamber partially filled with liquid and having a bubble which may be centralized within the chamber to level the indicator and, thus, the cassette holder 11. Suitable leveling means may be employed as is known to those skilled in the art.

With reference to FIG. 6, it is seen that the cassette holder 11 includes a top wall 37 and a bottom wall 35. In the central region of the cassette holder 11, a chamber 38 is defined between these walls 35 and 37.

Figure 7:
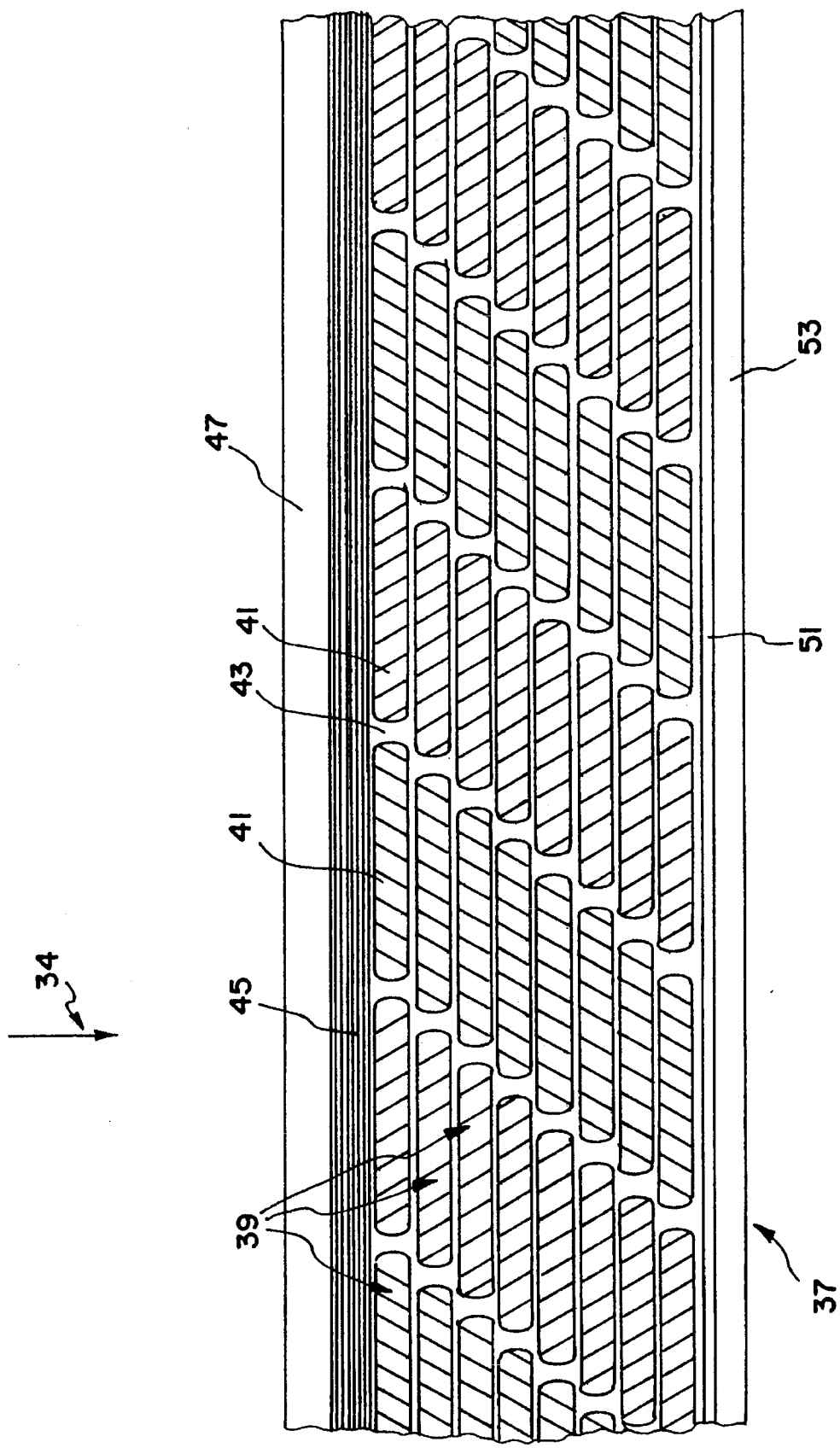
FIG. 7 shows a cross-sectional view along the line VII—VII of FIG. 6.

FIG. 7 shows a highly enlarged cross-sectional view of a portion of the top wall 37. As seen in FIG. 7, the top wall 37 includes a plurality of layers 39 of woven cloth, preferably made of graphite. As particularly seen in FIG. 7, each layer 39 of cloth is made up of flat ribbons 41 of graphite material having a generally rectangular cross-section and with extremely small air gaps 43 between adjacent ribbons 41. In fact, in practice, it has been found that these air gaps 43 are virtually non-existent. As should be understood from FIG. 7, there is virtually no linear air gap from the top of the layers of graphite cloth to the bottom thereof. Certainly, there is no single air gap, whatsoever, extending perpendicular to the lateral direction of extension of the top wall 37. Thus, x-ray radiation traveling in the direction of the arrow 34 may easily pass through the layers of graphite material 39 with no air gaps to distort or disturb the clear image of the bone structure of the patient. Above the layers 39 of graphite cloth, a plurality of layers 45 of fiberglass cloth are provided which are then covered with a resin coating 47 to seal the various layers 39, 45. Similarly, beneath the lowest graphite cloth layer 39, a plurality of fiberglass layers 51 are provided which are covered with a layer of resin coating 53. It is important to so encapsulate the graphite cloth layers 39. In particular, graphite material is known for its potential for developing extremely thin, long splinters which may enter the pores of the skin of a person and cause great damage while, at the same time, being difficult to remove from the pores of the skin of a person. The encapsulation of the graphite cloth layers in the manner described protects those who may come into contact with the cassette holder 11 from injury.

With reference, now, back to FIG. 3, it is seen that the cassette holder 11 carries a pair of crossed straps 55 and 57. As is clear, these straps 55 and 57 cross centrally of the patient and in a region between the iliac crests 27 and 29 of the patient as clearly shown in FIG. 3.

Figure 5:
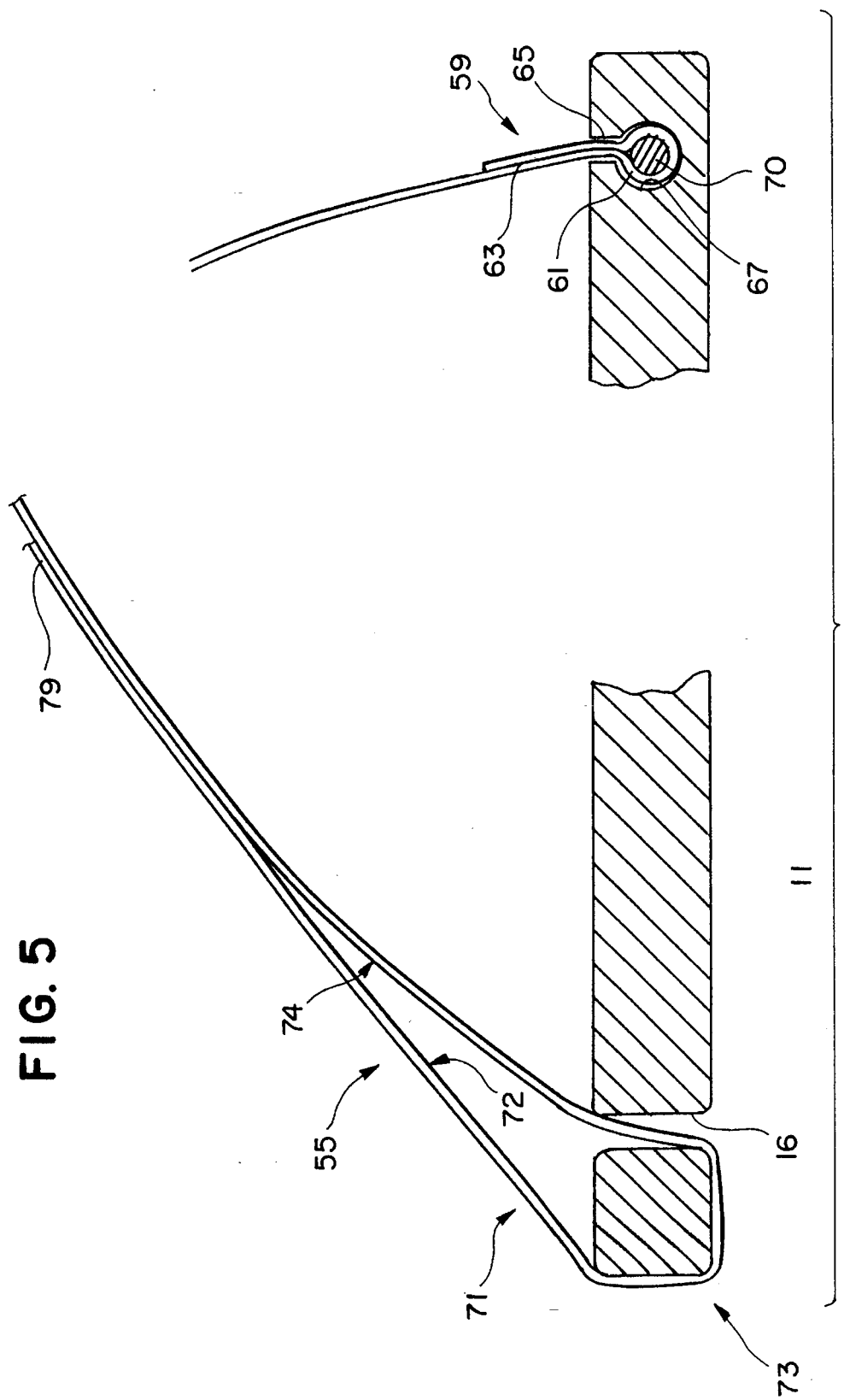
FIG. 5 shows a cross-sectional view along the line V—V of FIG. 3.

FIG. 5 shows particular details concerning the strap 55 which are representative of the strap 57 as well. In particular, it is seen that the strap 55 includes a first end 59 which includes a loop 61 formed by doubling back the material of the strap 55 upon itself and stitching at 63. The loop 61 is inserted through a narrow orifice 65 into a chamber 67 into which a pin 70 is laterally inserted to capture the loop 61 within the chamber 67 thereby capturing the end 59 of the strap 55 therein.

Figure 4:
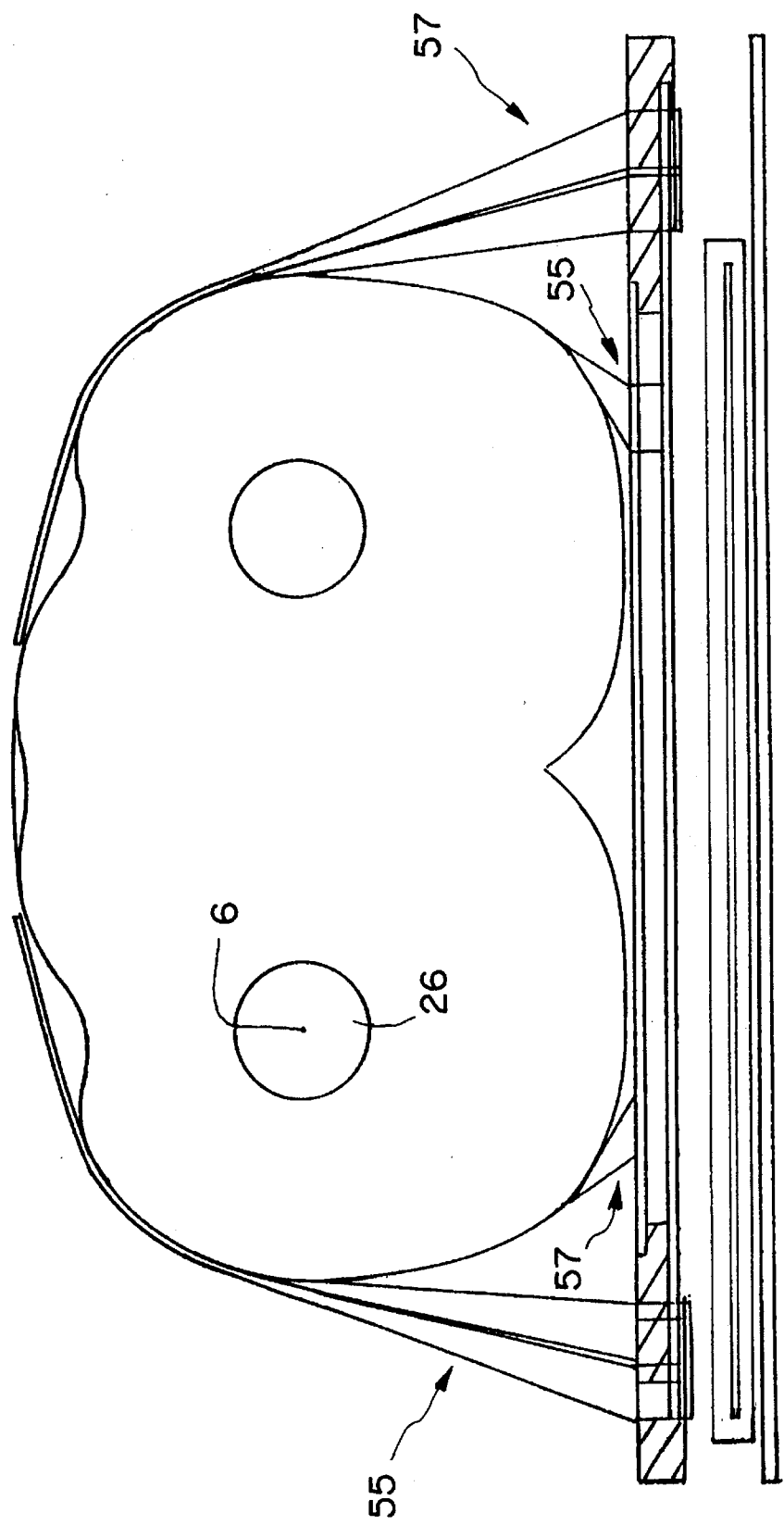
FIG. 4 shows a cross-sectional view along the line IV—IV of FIG. 3 including a cross-section through the patient.

The other end of the strap 55 is generally designated by the reference numeral 71 and is seen to include a further loop 73 which is made by extending the termination 75 of the strap 55 through a slot-like opening 16 in the cassette holder 11, extending the termination 75 under and around the cassette holder 11 and thence into engagement with itself as shown in FIG. 5. The surfaces 72 and 74 of the strap 55 are suitably covered with complementary halves, respectively, of hook and pile fastening material allowing infinite adjustment of the length of the strap 55 depending upon the particular anatomical dimensions of the particular patient. Thus, the strap 55 may be pulled through the slot 16 until the patient is tightly fixed to the cassette holder 11 whereupon the complementary hook and pile fastening surfaces 72 and 74 may be engaged with one another along a large area of the strap 55 to firmly affix the patient to the cassette holder 11. The details of the strap 57 are not described in detail herein but are identical to those which have been described hereinabove concerning the strap 55. FIG. 4 shows the straps 55 and 57 as affixed about the patient and as fastened to themselves as explained in FIG. 5 with respect to the strap 55.

With particular reference to FIGS. 1 and 2, the support arm 60 for the laser beam generating device and one of the radio-opaque scales will now be described. As shown, in FIG. 2, in particular, the cassette holder 11 includes a mount 77 having a recess 79 therein sized to receive an upstanding rod 80. The mount 77 includes a locking mechanism 81 which may, if desired, comprise a threaded rod 82 rotatable by gripping a knob 83 and received within a threaded recess within the mount 77 so that the knob 83 may be rotated to engage the end of the rod 82 with a side wall of the rod 80 to lock the rod 80 within the mount 77. With reference to FIG. 3, it is seen that a further mount 76 is also provided on the opposite side of the cassette holder 11 so that the rod 80 may be mounted on either side of the cassette holder 11 depending upon which side of the patient comprises the operation site.

With reference back to FIG. 2, it is seen that a base 85 is mounted on the rod 80 through a reciprocatory mount 86 including a passageway 87 therethrough sized to slidably receive the outer dimensions of the rod 80 and including locking means 88 similar in configuration, structure and function to the means 81 for locking the rod 80 within the mount 77. Thus, the position of the base 85 vertically with respect to the cassette holder 11 may be adjusted while, at the same time, the rotative position of the base 85 with respect to the rod 80 is fixed parallel to cassette holder walls 13 and 15 by a vertically elongated groove (not shown) in the rod 80 which receives the end of the threaded rod of the locking means 88.

FIG. 10 shows a visualization of indicia generally designated by the reference numeral 89 which, in fact, are displayed perpendicular to the view of FIG. 2 on the surface 84 of the base 85. These indicia 89 are rotated 90° from their actual position in the view of FIG. 10 so that they may be visualized. Similarly, the radio-opaque scale 31 contained within the cassette holder 11 and particularly depicted in FIG. 6 is also rotated 90° in FIG. 10 so that it may be visualized.

Figure 15:
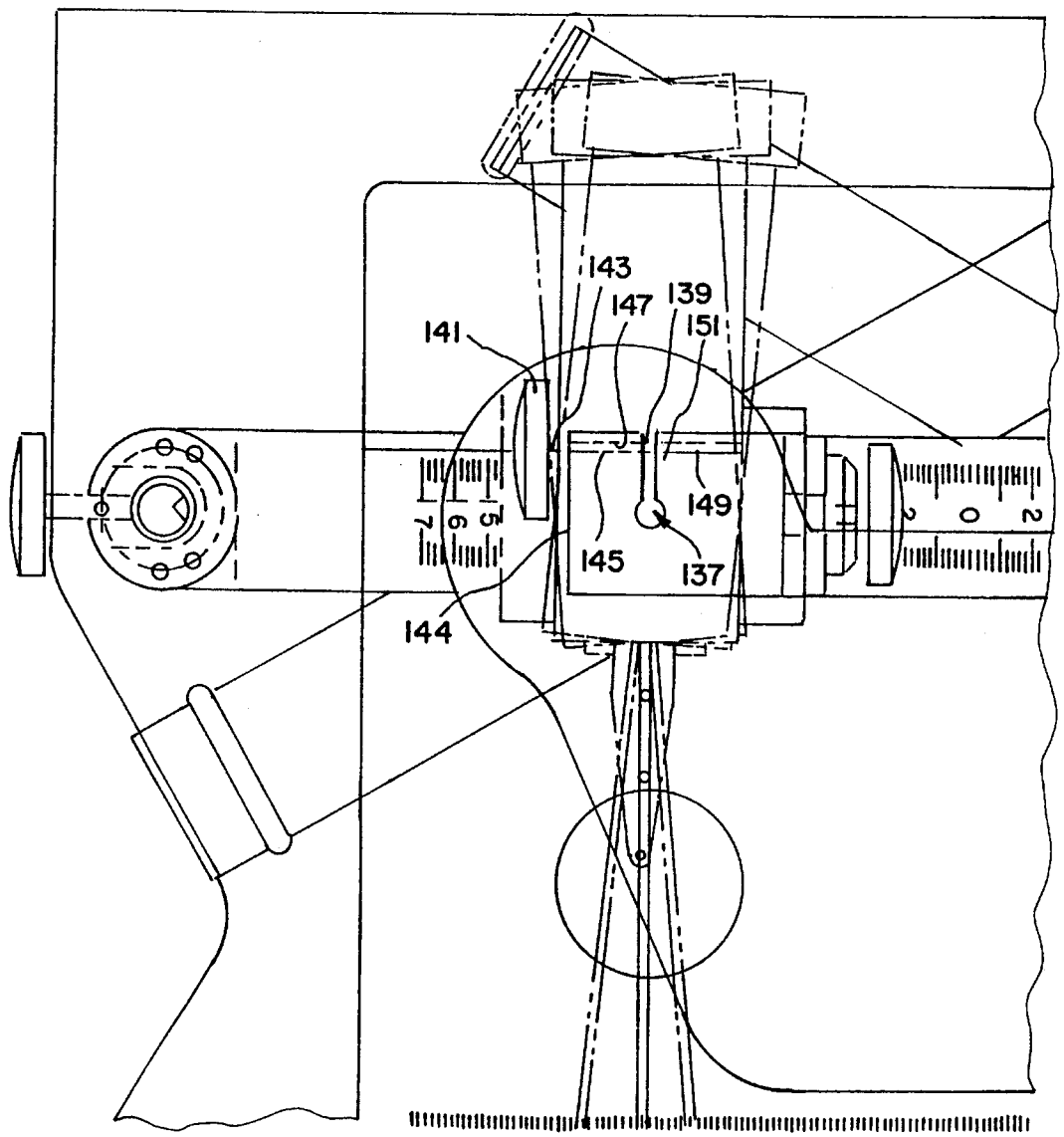
FIG. 15 shows an enlarged plan view of the invention with the laser beam generating device shown in phantom.

With further reference to FIG. 2, the base 85 carries a bracket 90 which includes an upstanding arm 91 having, at its upper end, an L-shaped bracket 92 designed to hold the laser beam generating device 100. The pointer 68 (FIG. 3) is carried by the bracket 90. The bracket 90 is slidably disposed on the base 84 so that its lateral position with respect to the base 84 may be suitably adjusted. The frictional sliding fit between the bracket 90 and the base 84 is provided so that the bracket 90 will be retained in any position to which it is moved. A locking knob 131 is also provided to suitably lock the position of the bracket 90. A knob 93 has a threaded rod 95 connected thereto which extends through the slot 133 in the arm 91 and is threadably received in the threaded hole 135 of the bracket 92. By loosening the knob 93, the bracket may be vertically adjusted to the extent of the slot 133 and the bracket may be rotated about the horizontal axis of the rod 95 to allow pivotable adjustment of the beam 150 about the horizontal axis. The locking means 88 may also be employed to adjust the vertical position of the laser beam generating device 100 with respect to the cassette holder 11. The bracket 90 may be moved with respect to the base 85 to provide lateral adjustment. The device 100 has a pin 124 extending downwardly therefrom (FIG. 2) through an opening 137 (FIG. 15) of the bracket 92. The opening 137 connects with a slot 139 that extends to the forward edge of the bracket 92. A locking knob 141 (FIG. 15) has a rod 143 extending therefrom having a smooth portion 145 slidably extending through smooth bore 147 across the slot 139. The rod 143 has a threaded end 149 threadably received in the threaded bore 151 which is across the slot 139 from the smooth bore 147 adjacent the knob 141, the rod 143 has a shoulder (not shown) which bears against the side wall 144 of the bracket 92. As such, when the knob 141 is rotated in one direction, the interaction between the threaded end 149 of the rod 143 and the threaded bore 151, and the rod shoulder (not shown) bearing against the side wall 144 of the bracket 92 causes the slot 139 to narrow, thus tightening the opening 137 about the pin 124 to lock its position therein. Rotation of the knob 141 in the opposite direction loosens the pin 124. Thus, the direction of emanation of the beam 150 may be suitably adjusted about the vertical axis of the pin 124. In this way, the beam 150 emanating from the laser beam generating device 100 may be suitably aligned and adjusted in all degrees of freedom to the position particularly shown in FIGS. 1 and 2 wherein a plane of light emanates from the lens assembly (to be described in greater detail hereinafter) of the laser beam generating device 100 and may provide a line of light along the mechanical axis of the leg 5 of the patient 4.

Figure 8:
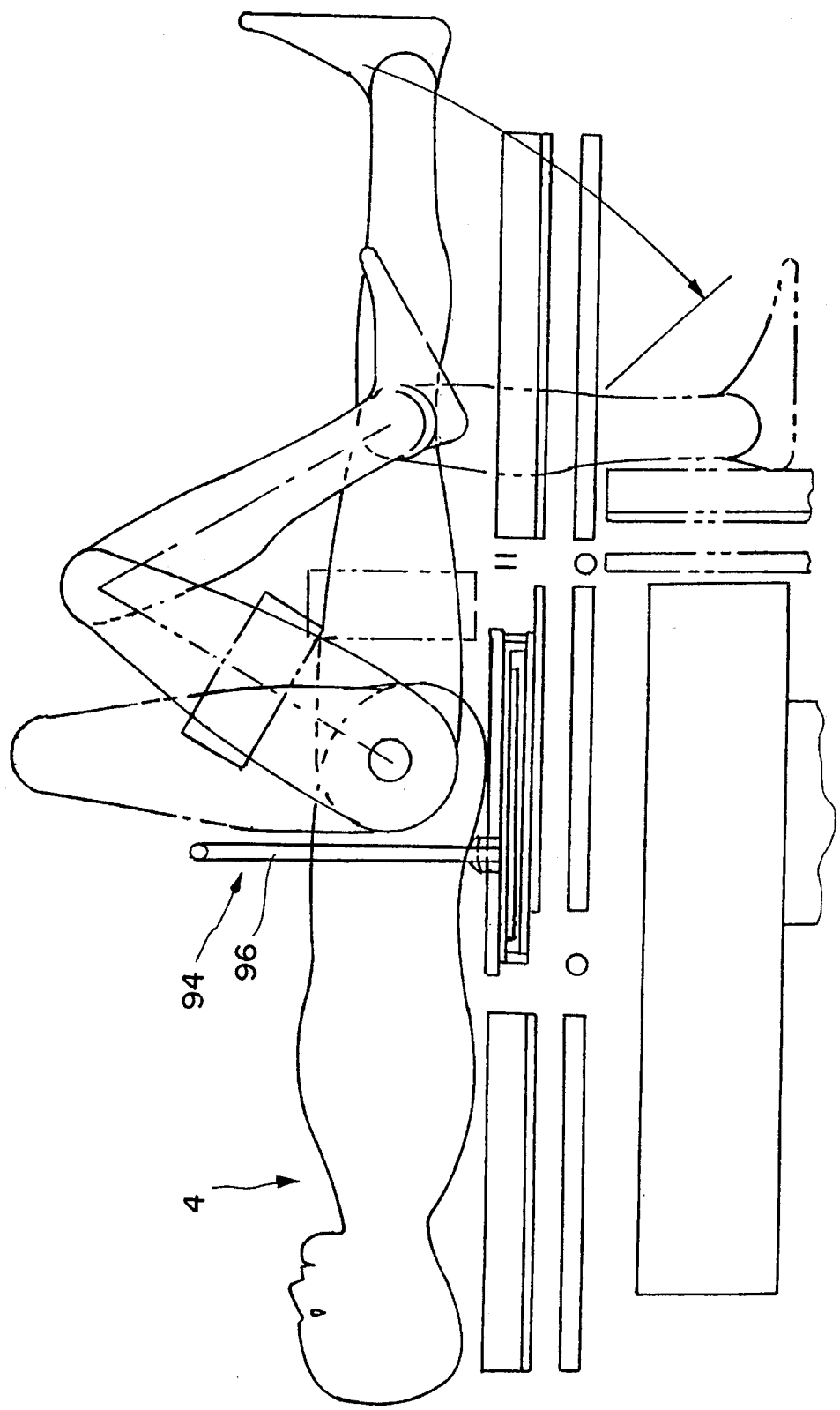
FIG. 8 shows a side view of the present invention similar to the view of FIG. 1 but showing the laser beam generating device and supporting bracket replaced with an L-shaped locating rod.
Figure 9:
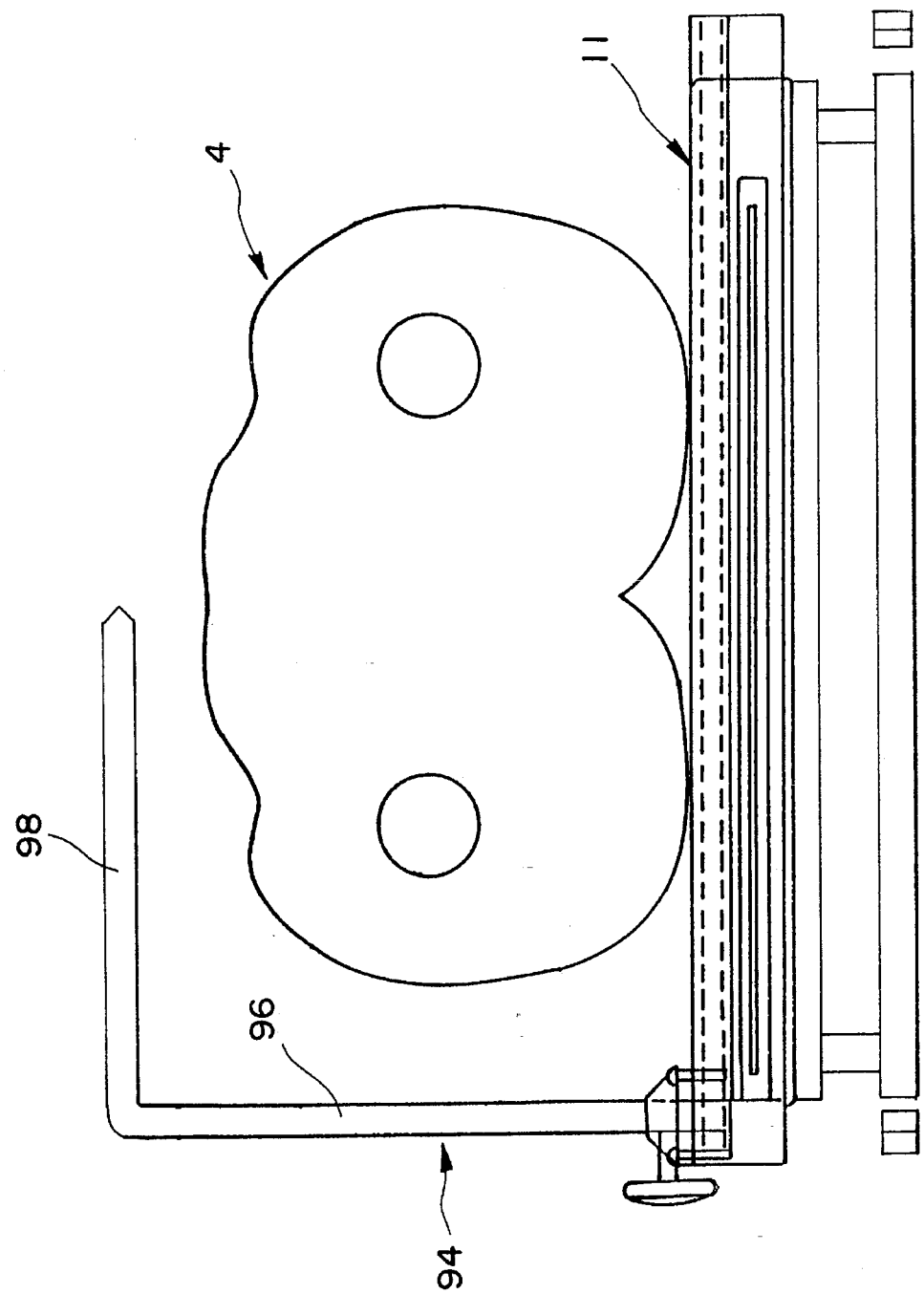
FIG. 9 shows an end view similar to that of FIG. 2 but showing the L-shaped locating rod also shown in FIG. 8.

With reference to FIGS. 8 and 9, the hubs 77 and 76 which are employed, during surgery, to support the rod 80 and associated structure, are also suitably employed to support a locating rod 94 which consists of an upstanding rod 96 and a right-angle extension 98. As will be described in greater detail hereinafter, the locating rod 94 is provided to allow initial positioning of the patient 4 on the cassette holder 11 before the straps 55, 57 are applied to affix the patient onto the cassette holder 11. Once the patient 4 has been properly located on the cassette holder 11 and the straps 55 and 57 have been suitably applied and tightened, the locating rod 94 is removed from the cassette holder 11 and is replaced with the upstanding rod 80 so that surgery can commence.

With reference, now, to FIGS. 11–14, the laser beam generating device 100 is seen to include a cylindrical housing 101 having a posterior removable cap 103 and defining an internal chamber 105. In the posterior end of the chamber 105, a laser beam generator 107 is mounted. The chamber 105 has an internal configuration sized to receive the laser beam generator 107 in only a single properly aligned configuration so that it may easily be installed therein in reproducible fashion. The laser beam generator 107, in the preferred embodiment of the present invention, employs a low-voltage class 3A diode crystal. Applicants have found that employing a wavelength of 635 nanometers or less provides a brilliant red light beam. The laser beam generator 107 is provided with a solid-state regulator that regulates the voltage thereof to 4½ volts even though the power source may be of higher voltage. Applicants have found that such a solid-state regulator in conjunction with a portable power source provides 6 to 8 hours of even, brilliant line demarcation that does not diminish in power throughout the operative case. The laser beam generator 107 is commercially available.

Forward of the laser beam generator 107 is a lens system 109 which is also commercially available and converts the thin cylindrical beam of light emanating from the laser beam generator 107 to a plane of light 150. The plane of light 150 is seen in FIG. 11 from above to be extremely thin and planar in configuration, approximately 1 millimeter in width. FIG. 12 shows the side of the plane of light 150 and shows the plane diverging at an angle of approximately 30°. As shown in FIGS. 11 and 12, the lens system 109 is recessed within the housing 101, for example, one inch, to preclude the user from being injured by looking directly at the beam from too close a distance.

The chamber 105 includes a small inlet orifice 111 connected to the adjacent atmosphere through a fitting 113. The chamber 105 also includes an orifice 115 much larger in area than the area of the orifice 111 and including a fitting 117 connectable through a conduit (not shown) to a source of vacuum.

When the housing 101 and the cap 103 are autoclaved to sterilize them, they are suitably dried. However, as is usually the case, at least a small amount of water or water vapor remains within the chamber 105. The laser beam generator 107 generates a significant amount of heat, in operation, and such heat vaporizes any residual water within the chamber 105 causing a clouding cover of water vapor to coat the lens system 109, thereby obscuring the laser beam emanating from the laser beam generator 107 and rendering inaccurate and fuzzy the resultant plane of light 150. Applicants have found that by connecting the chamber 105 to a source of vacuum, the water vapor contained within the chamber 105 may be suitably evacuated. At the same time, any bacterium contained within the chamber 105 is also evacuated and is prevented from infecting the patient. If any small cracks or orifices are located within the cylinder 101 in various locations including the mount of the lens system 109, between the cap 103 and the cylinder 101, etc., the negative pressure induced by the source of vacuum (not shown) will prevent the bacterium from leaving the chamber 105 at any other location save for the orifice 115 and fitting 117.

As is also known, the negative pressure which is created by connecting the orifice 115 to a source of vacuum while the smaller orifice 111 allows admittance of atmospheric air also reduces the latent heat of vaporization thereby providing a cooling effect which allows condensation and subsequent removal of any water vapor contained within the chamber 105. Additionally, the flow of air through the chamber 105 from the inlet orifice 111 through the chamber 105 and out the outlet orifice 115 provides a heat exchange effect with the air absorbing heat from the laser beam generator 107 and carrying the heat from the chamber 105 via the outlet orifice 115.

Thus, the laser beam generating system 100 is a completely self-contained unit which provides conversion of a cylindrical laser beam to a planar beam, which provides a sterile outer casing and a vacuum system designed to maintain sterility at the surgical site while, at the same time, cooling the entire device 100. In a further aspect, it is critical that the cooling effect of the vacuum system be operative throughout the surgical procedure. In this regard, were the cooling system not to be employed, the heating caused by the laser beam generator 107 will result in expansion of the mounting structure 91, 92, 93 and 95, the lens system 109, and other aspects of the system 100, thereby causing inaccuracies in the direction of emanation of the beam 150 including the possibility of beam "wander".

With the present invention now having been described in great detail, a method of performing surgery employing the inventive system will now be described in detail. The surgical method chosen in the example to be described below is that of a total knee arthroplasty. The method is as follows:

The central foam pad on the operating table is removed and replaced with the inventive x-ray cassette holder 11. The patient is then brought into the room and placed on the table in the exact position where, when the patient's operative knee is positioned to 90°, it strikes the locating rod 94 that extends from the lateral side of the cassette. This is the proper location for the patient. The straps 55, 57 emitting from the midportion of the cassette holder 11 at angles are then strapped over the iliac crest 27, 29 and then back onto the cassette in a snug manner (FIG. 5). This will fix the patient rigidly to the cassette holder 11. The patient's leg 5 is then prepared and draped as usual. The L arm-base 60 on the lateral aspect of the x-ray cassette is located by palpation through the drapes (not shown). A small slit is made with sterile scissors through the outer drape and the L arm extension rod 80 is passed on to the circulating nurse who in turn fixes it into the L arm base hub 77 or 76 on the cassette holder 11 and tightens it rigidly. A sterile towel (not shown) is passed about the L arm and fixed rigidly with a towel clip (not shown) to maintain sterility of this hole in the drape. With palpation the surgeon determines the approximate location of the patient's femoral head and adjusts the L arm locating device 68 to that location. If desired, a first x-ray is taken from the side of the patient and the resultant x-ray image is studied to determine the vertical distance from the lower radio-opaque scale 31 to the center 6 of the femoral head 26 and the vertical distance from the center 6 of the femoral head 26 to the upper radio-opaque scale 89. Thereafter, the elevation of the base 85 is vertically adjusted by manipulation of the locking means 88 to equalize these distances. A second x-ray is then taken with the x-ray head directly above the tip of the locating device. While the x-ray is being developed, the surgeon may proceed with the operation. When the x-rays return to the operative suite, the x-ray technician measures the location of the femoral head parallel to the top scale and parallel to the bottom scale and takes the mean of those two scales and tells the physician the proper location of the locating arm. In the meantime, the circulating nurse has turned on the laser and properly placed the laser into the sterilized laser cannister. The operative technician then applies the vacuum hose and places the laser bracket over the locating arm base and tightens the two knobs firmly.

The laser is now ready to be calibrated. The up and down knob on the laser cannister is released and the cannister is directed down at the femoral head locating arm. The left and right knob is released and the light is calibrated so that the beam strikes the correct predetermined number on the radio-opaque scale and also extends through the center line of the pointer arm. This knob is then firmly tightened. Medial-lateral alignment is now provided.

The doctor from this point on must align the patient's leg to this laser alignment rather than the laser being aligned to the leg. This procedure eliminates a cephalad, caudad error if the patient's hip should move. The laser is then adjusted by the up and down knob to cause the planar beam to strike the midportion of the thigh and extend all the way to the ankle with the knee extended. The resection cuts are then made on the distal femur and proximal tibia with the preferred instrumentation. The surgeon then abuts the resection cuts firmly together and aligns the knee on the laser beam. The proper alignment is when the beam goes through the exact center of the femoral knee and strikes the midportion of the ankle. If the laser line is striking the midportion of the ankle but is medially deviated 6 mms., the patient's alignment is in 1 degree of varus and if it is laterally deviated 6 mms. from the center of the knee, it is in 1 degree of valgus. Appropriate correction can be made at this time with additional resection. Trial components can then be applied and when firmly compressed together again, the alignment can be checked, and if it is not correct, it can be adjusted. Finally, if methyl methacrylate cement is being used on the procedure, absolute correct alignment can be obtained by maintaining the rigid compression of the components during the procedure with the laser beam extending through the midportion of the knee and the midportion of the ankle.

Accordingly, an invention has been described in terms of a preferred embodiment thereof as well as a preferred method of utilizing same, which fulfill each and every one of the objects of the invention as set forth hereinabove and provide a new and useful surgical laser beam-based alignment system and method of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

We claim:
1. A surgical alignment device, comprising:
a) a cassette holder adapted to be placed upon a patient supporting surface in underlying relation to a patient;

b) a pair of straps attached to said cassette holder, said straps being adapted to fixedly fasten a patient to said cassette holder;

c) a rod on one side of said cassette holder extending generally vertically therefrom, said rod carrying a base, said base carrying a pointer adjustable thereon;

d) a bracket on said base for supporting a light beam generating device for generating a visible light beam, said bracket including adjustment means for adjusting orientation of said light beam generating device with respect to a patient, said light beam generating device generating a thin planar beam adapted to display an elongated line of visible light on a patient to permit determination of proper patient alignment for performance of surgery.

2. The device of claim 1, wherein said cassette holder is made of a material which is transparent to x-rays.

3. The device of claim 2, wherein said material comprises graphite.

4. The device of claim 3, wherein said cassette holder is made of a plurality of layers of woven graphite cloth covered with fiberglass cloth and resin.

5. The device of claim 4, wherein said layers are stacked in laterally staggered relation so that, in a direction perpendicular to a direction of lateral extent of said layers, no air gaps are present.

6. The device of claim 1, wherein said cassette holder includes a radio-opaque scale embedded therein.

7. The device of claim 6, wherein said base carries a further radio-opaque scale with indicia aligned with corresponding indicia in the first-mentioned radio-opaque scale, whereby when an x-ray image is taken, compensation may be made for parallax error and said pointer may be accordingly moved to a position directly overlying a center of a patient's femoral head.

8. The device of claim 7, further including means for vertically adjusting said base on said rod whereby said further radio-opaque scale may be vertically adjusted to be a distance above a center of a patient's femoral head equal to a distance with which said first-mentioned radio-opaque scale is below said center, to further compensate for parallax error.

9. The device of claim 1, wherein said rod is connected to said cassette holder with a recess therein, said cassette holder having a further recess on an opposite side thereof permitting said rod to be inserted therein whereby said device may be employed for surgery to either side of a patient.

10. The device of claim 9, further including a locating rod, removably insertable in said recess or further recess, said locating rod being employed to accurately place a patient on said cassette holder.

11. The device of claim 10, wherein said locating rod is L-shaped.

12. The device of claim 1, wherein said cassette holder has a side wall with a notch therein permitting easy gripping of an x-ray film cassette.

13. The device of claim 1, wherein each strap includes a first end received in a first slot in said cassette holder, a second end extending through a second slot in said cassette holder and said second end being doubled back upon itself and fastened.

14. The device of claim 13, wherein facing doubled back faces of said second end of each strap carry respective halves of hook and pile fastening means.

15. The device of claim 1, wherein said light beam generating device comprises:

a) a light beam generator adapted to generate a thin cylindrical light beam;

b) a lens system adapted to convert said thin cylindrical light beam to a thin planar light beam; and c) a sterile housing enclosing said light beam generating device and lens system within a housing chamber therein.

16. The device of claim 15, wherein said light beam comprises a laser beam.

17. The device of claim 16, wherein said laser beam exhibits a wavelength of 635 nanometers or less.

18. The device of claim 15, wherein said housing includes an orifice connecting said housing chamber with atmosphere.

19. The device of claim 18, wherein said housing includes a port connected to a source of vacuum.

20. The device of claim 19, wherein said port has a larger area than said orifice, whereby negative pressure may be maintained within said housing chamber to prevent contamination of a patient by bacterium therein, said negative pressure cooling said housing chamber to condense and remove any vapor therein.

21. The device of claim 15, wherein said lens system is recessed within said housing.

22. The device of claim 1, wherein said adjustment means permits adjustment of said light beam generating device laterally and pivotably about horizontal and vertical axes.

23. The device of claim 1, wherein said cassette holder carries a level indicator.

24. The device of claim 23, wherein said level indicator comprises a bubble level.

25. The device of claim 1, wherein said pointer is mounted on said bracket.

* * * * *